United States Patent
Martens, III et al.

(10) Patent No.: US 7,213,770 B2
(45) Date of Patent: May 8, 2007

(54) VOLATILE MATERIAL DISPENSING SYSTEM

(75) Inventors: Edward J. Martens, III, Racine, WI (US); Stephen B. Leonard, Franksville, WI (US); Heather R. Schramm, Whitewater, WI (US); Kara L. Lakatos, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/881,816

(22) Filed: Jun. 30, 2004

(65) Prior Publication Data

US 2006/0000923 A1    Jan. 5, 2006

(51) Int. Cl.
*A24F 25/00* (2006.01)
(52) U.S. Cl. .............. 239/57; 239/34; 239/53; 239/55; 239/60; 428/905; 206/484.1
(58) Field of Classification Search .............. 239/34, 239/53, 54, 55, 56, 57, 60; 248/346.01, 163.1, 248/688; 206/0.5, 484.1; 428/905; 40/725, 40/746
See application file for complete search history.

(56) References Cited

U.S. PATENT DOCUMENTS

| | | |
|---|---|---|
| 882,710 A | 3/1908 | Pearsall |
| 886,840 A | 5/1908 | Mueller |
| 1,204,934 A | 11/1916 | Burford et al. |
| 1,261,133 A | 4/1918 | Kidd |
| 1,802,999 A | 4/1931 | Budd |
| 2,268,529 A | 12/1941 | Stiles |
| 2,469,656 A | 5/1949 | Lienert |
| 2,550,954 A | 5/1951 | Benedict |
| 2,577,320 A | 12/1951 | Fenyo |
| 2,579,715 A | 12/1951 | Wilson et al. |
| 2,779,624 A * | 1/1957 | Friedman ............ 239/54 |
| 2,840,689 A * | 6/1958 | Kazor ............ 40/441 |
| 3,178,844 A | 4/1965 | Christian |
| 3,424,380 A | 1/1969 | Curran |
| 3,558,055 A * | 1/1971 | Storchheim ............ 239/54 |
| 3,741,711 A * | 6/1973 | Bryant ............ 431/125 |
| 3,790,081 A * | 2/1974 | Thornton et al. ............ 239/55 |
| 3,804,330 A | 4/1974 | Miller, Jr. et al. |
| 3,948,445 A | 4/1976 | Andeweg |
| D243,402 S | 2/1977 | Irving |

(Continued)

FOREIGN PATENT DOCUMENTS

EP    0 645 081    7/2001

(Continued)

OTHER PUBLICATIONS http://www.glade.com/piso.asp.

(Continued)

*Primary Examiner*—Steven J. Ganey
(74) *Attorney, Agent, or Firm*—McCracken & Frank, LLP

(57) ABSTRACT

A volatile material dispensing system with a dispenser for providing controlled release of a volatile material, the dispenser being attached to a display frame, and having at least one protrusion. Protrusions are disposed on a face of the frame to distance the membrane from a delicate surface. The system prevents and/or hinders concentration of volatile material gases that could harm a delicate surface and resists tipping from a substantially vertical position.

35 Claims, 9 Drawing Sheets

U.S. PATENT DOCUMENTS

| | | | |
|---|---|---|---|
| 4,009,384 A | 2/1977 | Holland | |
| D247,573 S | 3/1978 | Schimanski | |
| 4,101,720 A * | 7/1978 | Taylor et al. | 523/126 |
| 4,157,787 A | 6/1979 | Schwartz | |
| 4,158,440 A | 6/1979 | Sullivan et al. | |
| 4,165,573 A | 8/1979 | Richards | |
| 4,170,080 A | 10/1979 | Bergh et al. | |
| 4,173,604 A | 11/1979 | Dimacopoulos | |
| 4,184,099 A | 1/1980 | Lindauer et al. | |
| 4,293,095 A | 10/1981 | Hamilton et al. | |
| D263,334 S | 3/1982 | Schimanski | |
| 4,327,056 A * | 4/1982 | Gaiser | 239/57 |
| D271,359 S | 11/1983 | Le | |
| D275,223 S | 8/1984 | Marxen | |
| D275,700 S | 9/1984 | Marxen | |
| 4,476,171 A | 10/1984 | Takeuchi | |
| 4,493,011 A | 1/1985 | Spector | |
| D279,146 S | 6/1985 | McCaffrey | |
| D280,363 S | 9/1985 | Wisecup, Jr. | |
| 4,549,250 A | 10/1985 | Spector | |
| 4,580,581 A | 4/1986 | Reece et al. | |
| D288,003 S | 1/1987 | Hoyt | |
| 4,695,435 A | 9/1987 | Spector | |
| 4,714,984 A | 12/1987 | Spector | |
| 4,720,409 A | 1/1988 | Spector | |
| D296,957 S | 8/1988 | Gordon et al. | |
| 4,762,275 A | 8/1988 | Herbert et al. | |
| 4,794,714 A | 1/1989 | Weisgerber | |
| 4,809,912 A | 3/1989 | Santini | |
| 4,814,212 A | 3/1989 | Spector | |
| 4,849,606 A | 7/1989 | Martens, III et al. | |
| 4,874,129 A | 10/1989 | DiSapio et al. | |
| 4,883,692 A | 11/1989 | Spector | |
| 4,898,328 A | 2/1990 | Fox et al. | |
| 4,913,349 A | 4/1990 | Locko | |
| 4,917,301 A * | 4/1990 | Munteanu | 239/57 |
| 4,921,636 A | 5/1990 | Traas | |
| 4,939,858 A | 7/1990 | Dailey | |
| 4,993,177 A | 2/1991 | Hudson | |
| 4,995,555 A | 2/1991 | Woodruff | |
| D320,266 S | 9/1991 | Kunze | |
| 5,060,858 A | 10/1991 | Santini | |
| D325,077 S | 3/1992 | Kearnes | |
| 5,148,983 A | 9/1992 | Muniz | |
| 5,148,984 A * | 9/1992 | Bryson et al. | 239/55 |
| 5,219,121 A | 6/1993 | Fox et al. | |
| 5,230,867 A | 7/1993 | Kunze et al. | |
| D339,238 S | 9/1993 | Hamilton | |
| 5,247,745 A | 9/1993 | Valentino | |
| 5,259,555 A | 11/1993 | Kiefer | |
| 5,297,732 A | 3/1994 | Hahn | |
| D346,068 S | 4/1994 | White | |
| 5,304,358 A | 4/1994 | Hoyt et al. | |
| 5,361,522 A | 11/1994 | Green | |
| 5,367,802 A | 11/1994 | Rosenberg | |
| 5,395,047 A | 3/1995 | Pendergrass, Jr. | |
| 5,402,517 A | 3/1995 | Gillett et al. | |
| D360,461 S | 7/1995 | Gillespie | |
| 5,439,100 A | 8/1995 | Gordon et al. | |
| D361,896 S | 9/1995 | Bramley et al. | |
| D366,107 S | 1/1996 | Shaffer | |
| 5,503,332 A | 4/1996 | Glenn | |
| D369,473 S | 5/1996 | Gluck | |
| 5,529,243 A | 6/1996 | Hoyt et al. | |
| 5,556,192 A | 9/1996 | Wang | |
| D376,002 S | 11/1996 | Upson | |
| D376,420 S | 12/1996 | Rymer | |
| 5,380,822 S | 7/1997 | Decker et al. | |
| 5,647,052 A | 7/1997 | Patel et al. | |
| 5,651,942 A | 7/1997 | Christensen | |
| D383,613 S | 9/1997 | Handler | |
| 5,679,334 A | 10/1997 | Semoff et al. | |
| 5,716,000 A | 2/1998 | Fox | |
| D392,032 S | 3/1998 | Zaragoza et al. | |
| 5,735,460 A | 4/1998 | Eisenbraun | |
| 5,744,106 A | 4/1998 | Eagle | |
| 5,749,519 A | 5/1998 | Miller | |
| 5,749,520 A | 5/1998 | Martin et al. | |
| 5,782,409 A | 7/1998 | Paul | |
| 5,788,155 A | 8/1998 | Martin et al. | |
| 5,804,264 A | 9/1998 | Bowen | |
| D399,298 S | 10/1998 | Whitehead | |
| 5,845,847 A | 12/1998 | Martin et al. | |
| 5,875,968 A | 3/1999 | Miller et al. | |
| 5,885,701 A | 3/1999 | Berman et al. | |
| D407,809 S | 4/1999 | Hammond | |
| 5,899,382 A | 5/1999 | Hayes et al. | |
| 5,950,922 A | 9/1999 | Flinn | |
| 5,961,043 A | 10/1999 | Samuelson | |
| 5,975,427 A * | 11/1999 | Harries | 239/34 |
| 6,031,967 A | 2/2000 | Flashinski et al. | |
| 6,065,687 A | 5/2000 | Suzuki et al. | |
| 6,106,786 A | 8/2000 | Akahoshi | |
| 6,109,537 A | 8/2000 | Heath | |
| D431,075 S | 9/2000 | Barraclough | |
| 6,144,801 A | 11/2000 | Lehoux et al. | |
| 6,152,379 A | 11/2000 | Sorgenfrey | |
| 6,154,607 A * | 11/2000 | Flashinski et al. | 239/34 |
| D435,100 S | 12/2000 | Pesu et al. | |
| D437,404 S | 2/2001 | Wu | |
| D439,964 S | 4/2001 | Wu | |
| D441,441 S | 5/2001 | Upson | |
| D445,262 S | 7/2001 | Rowan | |
| 6,254,248 B1 | 7/2001 | McAuley et al. | |
| 6,254,836 B1 | 7/2001 | Fry | |
| D451,990 S | 12/2001 | Millet | |
| 6,328,935 B1 | 12/2001 | Buccellato | |
| D453,561 S | 2/2002 | Nelson | |
| 6,354,710 B1 | 3/2002 | Nacouzi | |
| 6,358,577 B1 | 3/2002 | Bowen et al. | |
| 6,363,734 B1 | 4/2002 | Aoyagi | |
| 6,367,706 B1 | 4/2002 | Putz | |
| D456,888 S | 5/2002 | Buthier | |
| D461,006 S | 7/2002 | Buthier | |
| 6,435,423 B2 | 8/2002 | Hurry et al. | |
| 6,478,440 B1 | 11/2002 | Jaworski et al. | |
| 6,548,015 B1 | 4/2003 | Stubbs et al. | |
| 6,555,068 B2 | 4/2003 | Smith | |
| D476,726 S | 7/2003 | Rosenberg | |
| 6,610,254 B1 | 8/2003 | Furner et al. | |
| D479,742 S | 9/2003 | Hollingsworth | |
| 6,618,974 B2 | 9/2003 | Szalay | |
| 6,627,857 B1 | 9/2003 | Tanner et al. | |
| D481,113 S | 10/2003 | Groene et al. | |
| 6,631,852 B1 | 10/2003 | O'Leary | |
| 6,638,591 B2 | 10/2003 | Bowen et al. | |
| D481,785 S | 11/2003 | Koike | |
| 6,643,967 B1 | 11/2003 | Bloom | |
| 6,648,239 B1 | 11/2003 | Myny et al. | |
| 6,663,838 B1 | 12/2003 | Soller et al. | |
| D485,607 S | 1/2004 | Wu | |
| D487,308 S | 3/2004 | Engerant | |
| 6,705,541 B2 | 3/2004 | Schuehrer et al. | |
| 6,714,725 B2 | 3/2004 | Grone et al. | |
| 6,722,578 B2 | 4/2004 | Skalitzky et al. | |
| 6,730,311 B2 | 5/2004 | Maleeny et al. | |
| 6,749,672 B2 | 6/2004 | Lynn | |
| 6,790,436 B2 | 9/2004 | Williams et al. | |
| 6,808,791 B2 | 10/2004 | Curro et al. | |
| D498,524 S | 11/2004 | Morillas | |
| D498,525 S | 11/2004 | Harbutt et al. | |
| D498,836 S | 11/2004 | Morillas | |
| 6,998,581 B2 * | 2/2006 | Currie | 219/430 |
| 2001/0030243 A1 | 10/2001 | Hurry et al. | |

| | | |
|---|---|---|
| 2003/0007887 A1 | 1/2003 | Roumpos et al. |
| 2003/0017129 A1 | 1/2003 | Maleeny et al. |
| 2003/0089791 A1 | 5/2003 | Chen et al. |
| 2003/0094503 A1 | 5/2003 | Rymer et al. |
| 2003/0152374 A1 | 8/2003 | Grone et al. |
| 2003/0200690 A1 | 10/2003 | Galloway |
| 2004/0000596 A1 | 1/2004 | Cuthbert |
| 2004/0057975 A1 | 3/2004 | Maleeny et al. |
| 2004/0094636 A1 | 5/2004 | Channer |
| 2004/0135000 A1 | 7/2004 | Buthier |
| 2004/0262418 A1 | 12/2004 | Smith et al. |
| 2004/0262421 A1 | 12/2004 | Hurry et al. |
| 2005/0145711 A1 | 7/2005 | Blondeau et al. |

FOREIGN PATENT DOCUMENTS

| | | |
|---|---|---|
| EP | 1 346 734 | 9/2003 |
| GB | 3003643 | 11/2002 |
| GB | 3003644 | 6/2003 |
| GB | 3005817 | 7/2003 |
| GB | 3007046 | 9/2003 |
| GB | 3007049 | 9/2003 |
| GB | 3007052 | 9/2003 |
| GB | 3007053 | 9/2003 |
| GB | 3007054 | 9/2003 |
| GB | 3007055 | 9/2003 |
| GB | 3007056 | 9/2003 |
| GB | 3007057 | 9/2003 |
| GB | 3007233 | 9/2003 |
| GB | 3007045 | 10/2003 |
| GB | 3007048 | 10/2003 |
| GB | 3012024 | 2/2004 |
| GB | 3012025 | 2/2004 |
| GB | 3012026 | 2/2004 |
| JP | HA05015803 | 8/1993 |
| JP | D1027932 | 9/1998 |
| JP | D1195937 | 2/2004 |
| NL | 000194709-0001 | 9/2004 |
| NL | 000205661-0001 | 10/2004 |
| NL | 000252358-0001 | 2/2005 |
| NL | 000252366-0001 | 2/2005 |
| WO | WO 00/23121 | 4/2000 |
| WO | WO 03/068276 | 8/2003 |

OTHER PUBLICATIONS http://www.glade.com/plugins.asp.
http://www.airwick.us/product_page/product.html.
http://www.racerwheel.com/tcr-cz-103.html.
http://www.racerwheel.com/tcr-cz-102a.html.
http://www.giftsandgadgetsonline.com/ioairfrwilif.html.
http://www.allproducts.com/gifts/sundea1/02-ac105.html.
http://us.shop.com/cc.amos?main=catalog&pcd=783942&adtg=05180436&GA=1.
http://www.autobarn.net/skulrotairfr.html?AID=10274001&PID=613288.
http://www.negativeiongenerators.com/XJ-201ionicfreshener.html.
http://www.buylighting.com/Odor_eliminating_light_bulbs.html.
International Search Report & Written Opinion dated Sep. 12, 2005 Appl. No. PCT/US2005/023226.

* cited by examiner

VOLATILE MATERIAL DISPENSING SYSTEM

FIELD OF THE INVENTION

The invention generally relates to volatile material dispensers. More specifically, the invention relates to a liquid volatile material dispenser that utilizes a permeable membrane and prevents damage to delicate surfaces from the volatile material emanating from the membrane.

REFERENCES TO OTHER PENDING APPLICATIONS

This application is related to the following applications filed concurrently herewith: Volatile Material Expiration Indicating System, application Ser. No. 10/880,634 and Volatile Material Dispensing System with Illuminating Means, application Ser. No. 10/880,885.

BACKGROUND

A variety of methods have been utilized to contain volatile materials and permit controlled dispensing of these materials as vapors into the ambient air. The prior art describes in detail the use of permeable membranes, as well as other manners to dispense volatile material from a dispenser. A variety of volatile material dispensers have been designed to be positioned in various open and closed areas, dependent upon the particular need for the dispenser. The prior art also describes manners and devices for displaying the dispensers.

The prior art describes in detail volatile material dispensers that are designed to be affixed to surfaces with adhesives, plugged into electrical wall outlets, hung upon a variety of indoor/outdoor devices such as garbage pails, toilets, and the like. The prior art describes in further detail the use of permeable membranes utilized to dispense a volatile material and be positioned in various positions as described above.

U.S. Pat. No. 4,293,095 describes an air treating device in which an operative fluid is evaporated to effect the air treatment. U.S. Pat. No. 5,219,121 describes a device for dispensing any one of a wide range of volatile liquids as vapors and comprises a reservoir with an open end closed by a vapor-permeable, liquid-impermeable element. U.S. Pat. No. 6,722,578 describes a volatile material dispenser with a lid laminate that includes a vapor-permeable layer. U.S. Pat. No. 5,395,047 describes a repositionable device for delivery of volatile materials.

Specific to personal living spaces and professional office settings, there is a desire to make the ambient air more pleasing than it may be due to unpleasant odors that occur for a variety of reasons. There is also a desire for insect and pest control in these spaces and is an ongoing need. The prior art describes many such devices that may be employed for use in these spaces for both air freshening and insect control.

Due to the nature of the problem that is being combated, air treatment/freshening and insect control, there is a societal stigma associated with the presence of such noticeable devices within the personal living spaces and professional office settings where the devices may be employed. An unsightly or clearly identified device is not desirable in such settings. Rather, it is preferable that such a device be decorative and pleasant to the user and, more importantly, to individuals who may frequent the particular settings.

The volatile materials utilized for air freshening and insect repellant purposes often are comprised of destructive chemicals. Such chemicals are not designed for human consumption nor for direct or indirect contact with delicate or fine surfaces. Such chemicals in direct contact are destructive to delicate surfaces, and this is one of the reasons for utilizing a membrane based dispenser. However, the chemicals are diffused into the ambient air and have the potential for direct contact when in a gaseous state. Concentration of the volatile material gases also causes destructive affects to fine surfaces, but it is often necessary to place such dispensers in close proximity to delicate surfaces.

Personal and business settings often contain delicate surfaces. The prior art volatile material dispensers that utilize adhesives to adhere the dispenser to a surface may damage the surface. The surface may be damaged both by the adhesive and the proximity of the volatile material fumes to the delicate surface. Prior art dispensers may cause direct or close contact between a supporting surface and the volatile material emanating surface of the dispenser. This proximity causes marring and alteration of surfaces in a very short period of time. In some cases less than an hour, especially where there is no manner for distancing the emanating surface from the supporting surface.

The prior art does not describe a decorative volatile material dispenser that may be displayed and prominently positioned upon delicate surfaces as well as prevent or impede marring or alteration of the delicate and fine surfaces caused by contact with adhesives or proximity to volatile material fumes. Furthermore, a device that can be vertically or horizontally positioned with great ease while preventing or impeding the alteration of delicate surfaces is desired.

The present invention solves this problem by providing for a decorative volatile material dispenser that prevents unwanted repositioning of the dispenser and prevents damage, or dramatically increases the amount of time in which damage may occur, to delicate surfaces resulting from concentration of harmful volatile material fumes.

SUMMARY OF THE INVENTION

In accordance with a first aspect of the invention, a volatile material dispensing system is provided that includes a reservoir having a first surface and a vapor permeable membrane sealed to an outer periphery of the first surface and a volatile material contained within the reservoir. The volatile material is diffused through the membrane into an ambient atmosphere. The system also includes a planar frame. The reservoir is affixed to the rear face and a plurality of protrusions attached to one face of the frame, wherein the protrusions are configured to distance the membrane from a supporting surface when the frame is horizontally disposed. The protrusions also provide for an air passage sufficient to prevent volatile material gases from altering the supporting surface.

In accordance with a second aspect of the invention the protrusions are a set of two opposably positioned arcuate extensions attached to the frame. The arcuate extensions extend from one side wall to an adjacent side wall and are permanently attached to the frame. The bottom surface of the extensions is disposed in a planar relationship with a side wall of the frame.

In accordance with a third aspect of the invention the protrusions are four corner protrusions that provide an air passage between each protrusion. The protrusions have flat walls and curved side walls, the side walls are coplanar to the side walls of the frame.

In accordance with a fourth aspect of the invention, the protrusions are a set of four nodules proximal to each corner of a rectangular frame. The frame is held in place by a detention means that maintains the frame in a substantially vertical position.

In accordance with a fifth aspect of the invention, a volatile material dispensing system is provided with a reservoir having a first surface and a vapor permeable membrane sealed to an outer periphery of the first surface and a volatile material contained within the reservoir. The volatile material is diffused through the membrane into an ambient atmosphere. A planar frame having a front face and a rear face is also provided, and a reservoir is affixed to the rear face of the frame. Also included is a protrusion attached to the rear face of the frame, and the protrusion is configured to distance the membrane from a supporting surface when the frame is in a substantially horizontal position providing an air passage sufficient to impede volatile material gases from altering the supporting surface.

Other features will become apparent to those skilled in the art from a review of the following detailed description, taken in conjunction with the drawings and the appended claims. While the disclosed dispenser is susceptible of embodiments in various forms, described below are specific embodiments that are intended as illustrative (and not intended to limit the disclosure to the specific embodiments described herein).

DETAILED DESCRIPTION

Figure 1:
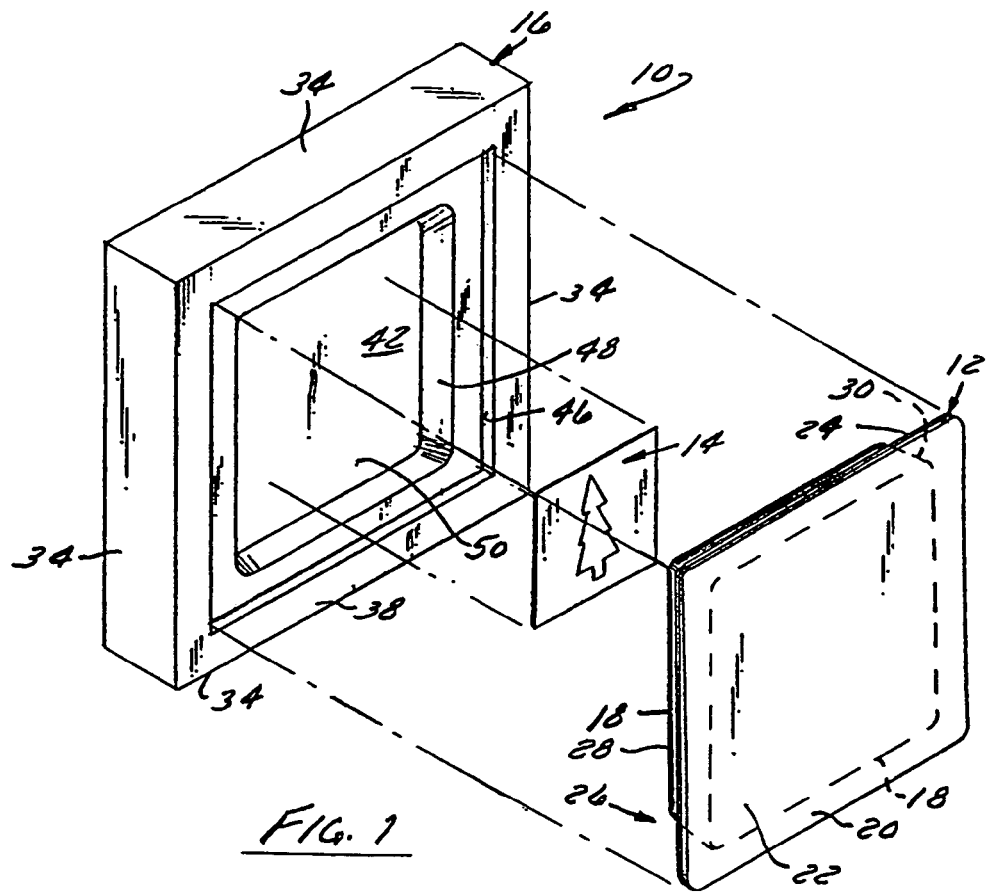
FIG. 1 is an exploded back perspective view of the system.
Figure 2:
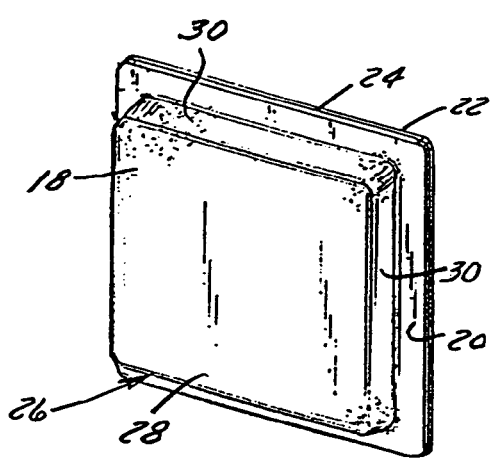
FIG. 2 is a perspective view of the blister as shown in FIG. 1.

Referring to FIGS. 1 and 2, a volatile material dispensing system 10 is illustrated, the system 10 having an evacuatable material dispenser 12, a decorative image 14, and a display frame 16 for holding the dispenser 12. The decorative image 14 is attached to the frame 16. The image 14 may be printed, formed, etched onto the surface and a silk screen image maybe utilized as well.

Figure 7:
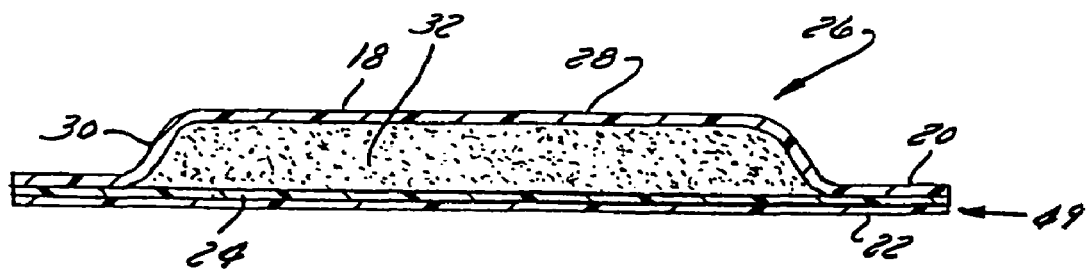
FIG. 7 is a partial enlarged sectional view of the system blister as shown in FIG. 6.

The dispenser 12 includes a blister 18, a peripheral flange 20, and an impermeable laminate 22 releasably adhered to said blister 18. The blister 18 includes a non-porous permeable membrane 24 comprised of low density polyethylene (LDPE), and a cup-shaped structure 26. Cup 26 includes a recycled polyethylene terephthalate (RPET) layer adhesively bonded to a nylon laminate. The nylon laminate includes a layer of ethylene vinyl acetate (EVA) coextruded to each side of a middle nylon layer. The cup 26 includes a bottom wall 28 and four side walls 30, that in conjunction with the membrane 24 acts as a sealed reservoir to contain the volatile material 32 (FIG. 7).

The laminate 22 includes a layer of polypropylene, aluminum foil, and polyester. The polypropylene is adhesively bonded to the aluminum foil layer, which is adhesively bonded to the polyester layer. An extrusion bonding material is used to bond the layers together. Laminate 22 preferably has a thickness of between 0.1 to 0.2 mm. The polyester layer is suitable for printing and is the outer surface of laminate 22. Preferably the membrane 24 and polypropylene layer of laminate 22 are coextruded when the blister is manufactured. The coextrusion permits for the laminate 22 to be peelably removed from the blister 18 while avoiding unnecessary reactions between an adhesive and the volatile material 32 during diffusion.

Cup 26 preferably has a thickness between 0.3 to 0.4 mm. The cup 26 is generally rectangular and preferably square with overall dimensions of about 3–5 mm thick, 50–60 mm long and 50–60 mm wide. Each of its four sidewalls 30 has a corresponding width of 3–5 mm and a length of 50–60 mm. Sidewalls 30 taper slightly outward as one moves from the bottom wall to the flange 20. Bottom wall 28 is also generally rectangular and has width of 48–58 mm and a height of 48–58 mm. The sidewalls 30 and bottom wall 28 of cup 26 are preferably thermoformed from a single sheet of the RPET and nylon laminate that is heated, then either blown or pressed into the flange-and-cup arrangement shown in the FIGURES. Preferably the cup 26 is clear and translucent, allowing for the visibility of the volatile material 32 contained within the blister 18.

The cup 26 contains relatively shallow side walls 30, as stated above. The shallow nature of the blister 18 allows for the membrane 24 to collapse upon the bottom wall 28. Diffusion of the volatile material 32 through the membrane 24 creates collapsing of membrane 24 upon wall 28 that maintains contact between the volatile material 32 and the membrane 24. The contact allows for a greater percentage of overall volatile material 32 diffusion and allows for indication of volatile material 32 expiration.

Peripheral flange 20 is preferably planar. It is coupled to and extends outward from the top edges of the cup 26 (e.g. the upper edges of sidewalls 30). Flange 20 is integrally formed with the cup 26 in a thermoforming process, as described in the preceding paragraph.

Following placement of the volatile material 32 into the cup 26, a seal is made between the flange 20 and the permeable membrane 24 thereby forming the dispenser 12.

At the same time laminate 22 may be attached to the blister 18 by having already been adhered to the membrane 24. The membrane 24 and laminate 22 may be attached to the flange 20 of the blister 18 using any conventional means, such as an adhesive, heat sealing, crimping, or the like. The seal must be air-tight so as to prevent leakage of air or volatile material 32. Most preferably the membrane 24 and the laminate 22 are sealed to the cup 26 in a single step. The volatile material 32 does not completely fill the void within the blister 18. A relatively small amount of air can be tolerated in dispenser 12 following the creation of blister 18. Preferably the air in the sealed blister is no more than 3–6% of the overall volume of the blister 18. As the volatile material diffuses out of dispenser 12 no air enters the blister 18 through the permeable membrane 24. The membrane 24 is configured to distend and collapse without the formation of gas bubbles.

When the volatile material is to be dispensed, the laminate 22 is removed from the blister 18. Preferably, the removal process will occur by a user grasping an end of the laminate 22 and peeling it off the blister 18. A tab, extension, or other means for grasping (not shown) may be included as an extension of the laminate 22 to aid in removal of the laminate 22. The extension may be at the corners, ends, or on the surface of the laminate 22.

Permeable membrane 24 has a thickness of about 0.05 to 0.06 mm and has a density preferably between 0.88 and 0.95 grams/cubic centimeter. It is formed integrally with laminate 22 and is heat fused to flange 20 such that membrane 24 extends across the entire cup 26. Membrane 24 encloses and seals the cup 26 with the volatile material 32 stored inside thereby forming a thin sealed container impermeable to the volatile material 32 stored inside. This container remains impermeable until the user grasps a corner of laminate 22 and peels laminate 22 from the membrane 24, thereby exposing permeable membrane 24 and permitting the volatile material 32 to migrate through the permeable membrane 24 and diffuse into the ambient air. The membrane 24 is preferably comprised of LDPE and is clear and translucent, allowing for visibility of the volatile material contained within the blister 18.

Frame 16 is a rectangular structure, preferably square, with four substantially equal-sized side walls 34, a front face 36 (FIG. 4) and a rear face 38. Frame 16 preferably has a thickness of between 12 and 22 mm and a height and width of between 70 and 90 mm. More preferably frame 16 has a width of approximately 15 mm and height of approximately 80 mm. The frame 16 should preferably have a surface area greater than 3000 mm$^2$. Side walls 34 are planar and perpendicularly disposed in relation to front face 36 and rear face 38. Alternatively, a draft may be present in the range of 3° outside to 3° inside with respect to the planar frame 16.

Figure 4:
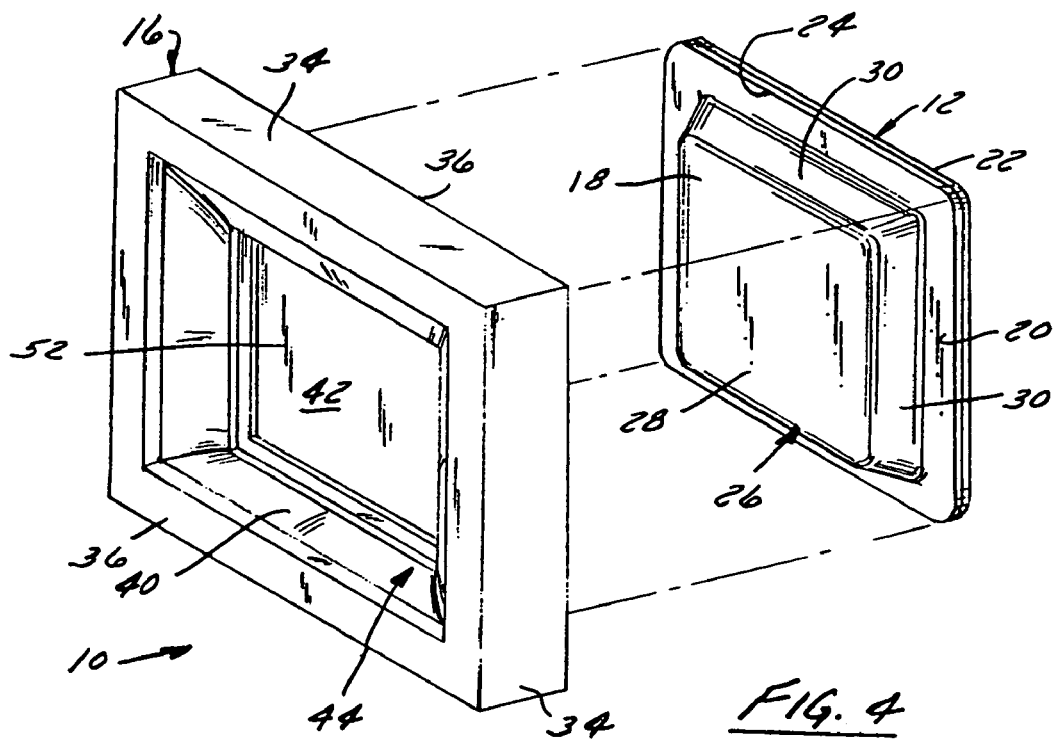
FIG. 4 is an exploded front perspective view of the system.
Figure 5:
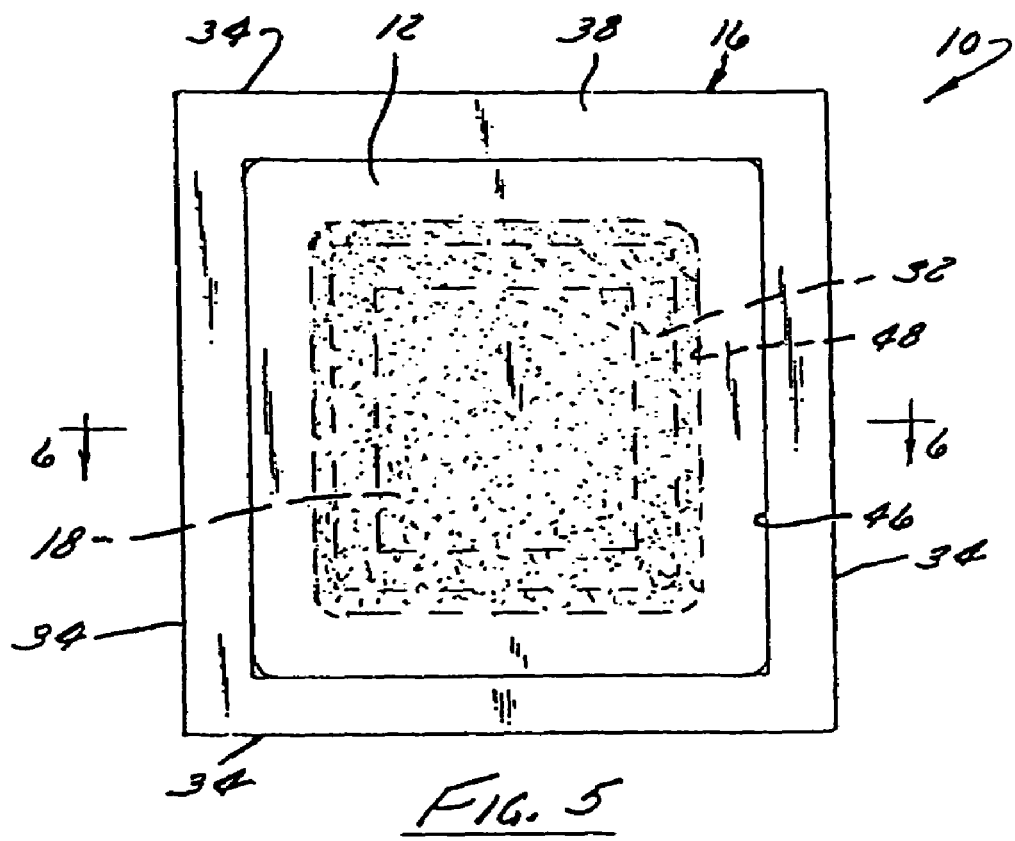
FIG. 5 is a rear face view of the system with a blister in the first filled condition.
Figure 6:
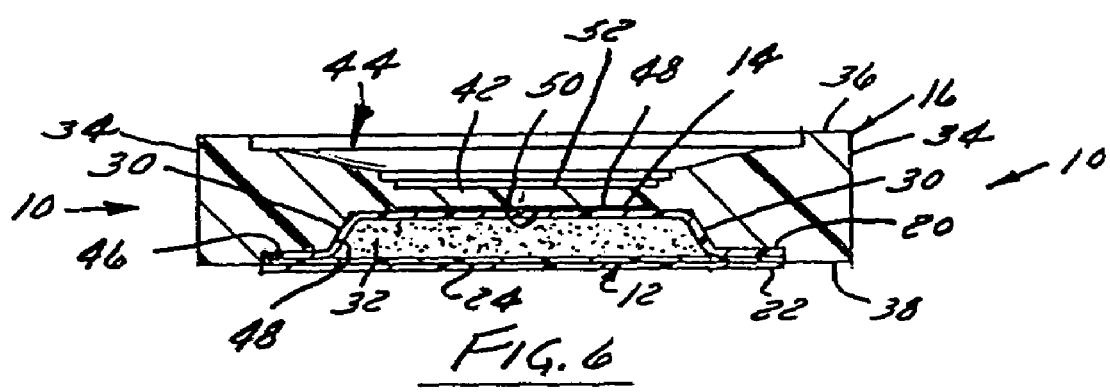
FIG. 6 is a sectional view taken substantially along line 6—6 of FIG. 5.
Figure 9:
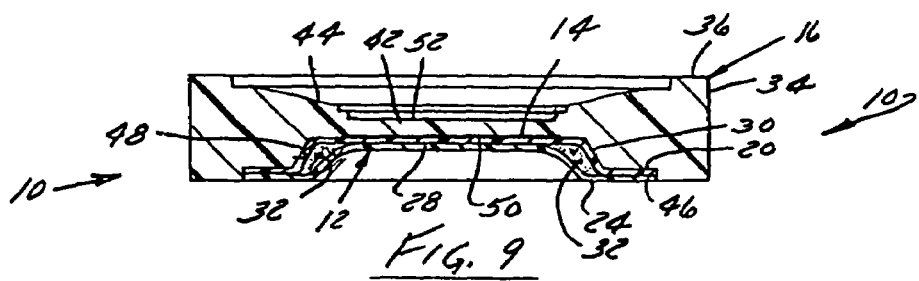
FIG. 9 is a sectional view taken substantially along line 9—9 of FIG. 8.
Figure 10:
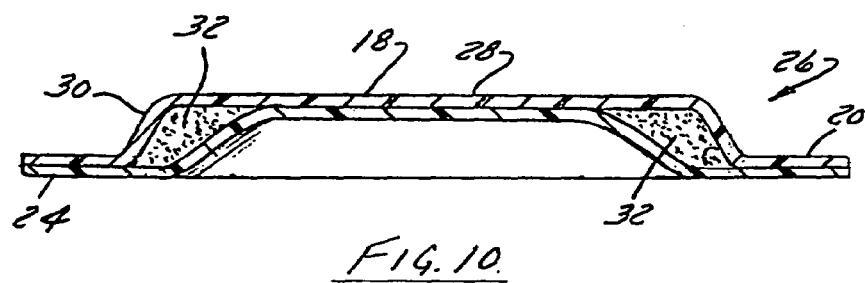
FIG. 10 is a partially enlarged sectional view of the system blister as shown in FIG. 9.
Figure 11:
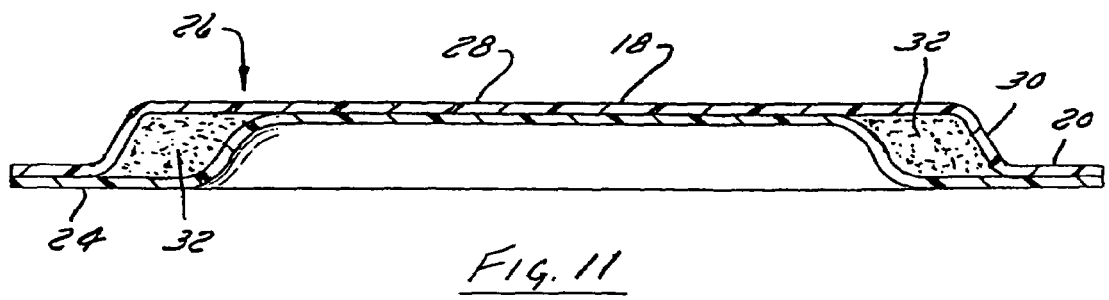
FIG. 11 is a partially enlarged sectional view of the blister alone taken substantially along line 11—11 of FIG. 8.

Front face 36 has a stepped recess 40 (FIG. 4). Recess 40 gives frame 16 the appearance of a picture frame surrounding and framing the bottom (or back) wall 42 (FIG. 4) of the recess 40. In the preferred embodiment, shown in FIGS. 6 and 9, the walls of recess 40 appear in cross section to have steps or curves 44 in the manner of an ornate picture frame. The recess 40 preferably centered in the front face 36 and is disposed away from the side walls 34. The recess 40 does not extend to the edge of the front face 36. Instead, front face 36 appears as a border extending around the edges of the recess 40, having a constant width between 2 and 4 mm.

Wall 42 is preferably transparent or translucent to permit light to pass through. Wall 42, in that regard, may function as a window that permits the viewer (from the front) to visually perceive what is directly behind wall 42.

Rear face 38 of frame 16 also is recessed. This recess is similarly stepped, and is configured to completely receive dispenser 12, with dispenser 12 positioned so that the membrane 24 surface is substantially flush with rear face 38. The recess is also preferably stepped, having a shallower peripheral recess 46 extending all the way around rear face 38 and a deeper central recess 48. The deeper central recess 48 is configured and dimensioned to receive cup 26, and the peripheral recess 46 is configured and dimensioned to receive and support flange 20. In short, the central recess 48 and peripheral recess 46 combined have a negative shape that is the same as that of dispenser 12.

Peripheral recess 46 preferably has an adhesive, spring clip, or other mechanical or adhesive retaining means that is configured to hold flange 20 in place. Flange 20 and peripheral recess 46 may be adhered to one another through the use of any adhesive, or alternatively though a mechanical means, such as interference fit, or separate mechanical fastener, such as a spring clip. When an adhesive 49 is used (as shown herein), a flange-to-frame adhesive may be chosen to either permanently adhere the flange 12 to the display frame 16 or, alternatively, be releasably adhered for easy removal. Preferably an ultra violet (UV) cured adhesive is used. In this manner, frame 16 can be a permanent and reusable item to which a succession of replacement dispensers 12 are affixed and later removed and replaced.

Central recess 48 is deeper than peripheral recess 46 since it must accommodate the greater combined thickness of cup 26, flange 20 and membrane 24. The bottom of cup 26 is adjacent to and preferably slightly spaced apart from the bottom 50 of central recess 46. Central recess 48 and peripheral recess 46 are preferably centrally spaced from the internal edges of rear face 38.

Figure 3:
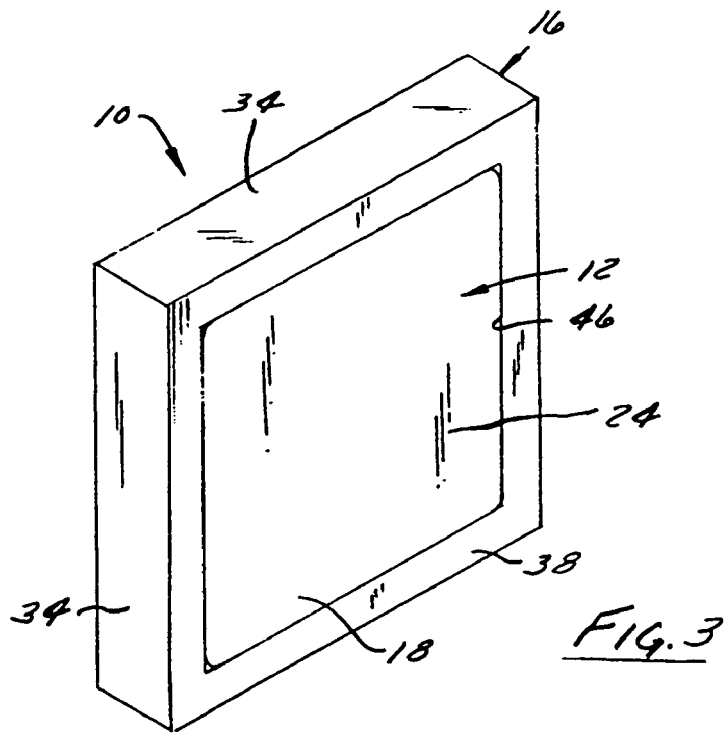
FIG. 3 is a perspective view of the assembled system as shown in FIG. 1.

The distance between the bottom 50 (FIG. 1) of central recess 48 and the bottom 52 (FIG. 4) of recess 40 on the front face 36 of frame 16 (i.e. the thickness of wall 44), is preferably between 2 and 5 mm. Wall 42 may be transparent or translucent. The translucent properties of wall 42 enables the user to easily identify when the volatile material 32 has nearly all diffused through membrane 24. Additionally, the translucent properties of wall 42 have a decorative function. The frame is best shown (FIGS. 3 and 4) to represent the translucent properties of wall 42.

The display frame 16 may be constructed from a variety of compositions, including glass, injection-molded plastic, or copolyester resin. In the preferred embodiment, the display frame 16 is constructed from molded glass that is clear and transparent.

Blister 18 of the dispenser 12 is filled with a volatile material 32. It is particularly suited for use in holding a volatile material 32 comprising an active ingredient, which is to be slowly diffused into the surrounding atmosphere, such as a fragrance, air freshener, insect repellant insecticide. In addition to the active ingredient the preferred embodiment includes a dye and thickening agent that color and thicken the volatile material 32. The dye and thickening agent most preferably comprise less than 2% of the overall composition.

Insecticides and other related chemicals may also be utilized as the volatile material 32. Where the user does not wish to have an unsightly insect repellant device, but requires the utility of a repellant, the decorative system is advantageous and blends in with the surrounding decor. The indicator system 10 allows for such a volatile material 32 to be released while having a decorative appearance.

When volatile material 32 is a fragrance, the fragrance can be relatively simple in composition, or can be a complex mixture of natural and/or synthetic chemical compounds.

Various mixtures of volatile materials for use in the indicator system may comprise as few as two chemicals and as many as over one hundred. Most conventional fragrance materials are synthetic or naturally derived volatile essential oils, such as, for example, lemon, mandarin, caraway, cedar leaf, clove leaf, cedar wood, oil of bergamot, bitter orange, geranium, lavender, orange, origanum, lavandin, neroli, rose absolute, cinnamon, and the like. Many of these materials may adversely affect treated surfaces on furniture. Synthetic types of fragrance composition, either alone or in combination with natural oils, are described in U.S. Pat. Nos. 4,314,915; 4,411,829; and 4,434,306, which are incorporated herein by reference.

Figure 8:
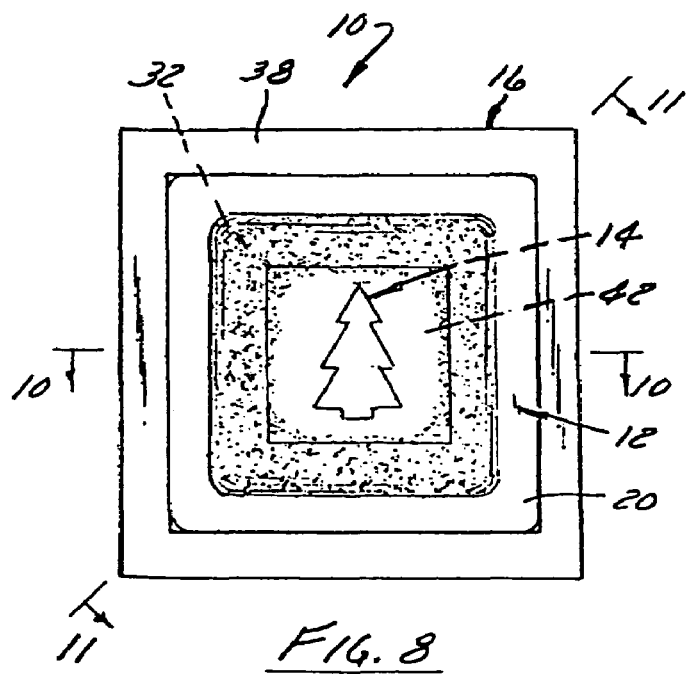
FIG. 8 is a front face view of the system with a partially evacuated blister.

The image 14 (FIGS. 1 and 8) may be graphic or textual. It may read, for example, "Please Replace." The image may be positioned in a plurality of positions, including but not limited to the following: front face 36 of frame, rear face 38 of frame, upon the permeable membrane 24, or upon the bottom wall 28 (FIG. 4). The image may be printed upon a layer of primed polyester that is adhesively adhered to the system 10, as described above. Alternatively, the image may be thermoformed into the bottom wall 28, molded into the decorative frame 16, or etched onto the frame 16.

The image 14 is shown in the shape of a tree, but may also be chosen from festive images used during various holiday seasons, such as a Christmas tree, menorah, Easter egg, valentine heart, pumpkin, and the like. Additionally, the color of the volatile material may be chosen in conjunction with such images to aid in celebration of the respective holidays. Multiple color combinations may be utilized in accordance to the decorative tastes of the user. The image 14 may be a plurality of other images that may include flowers, wildlife, cosmic displays, sporting related, and the like.

Depending upon the type and amount of dye utilized in conjunction with the volatile material 32 and the positioning of the image 14, either in front of or behind volatile material 32, the image 14 may or may not be viewable when the blister 18 is filled. Preferably the image is not viewable until a majority of the volatile material 32 has been released, and the dispenser 12 nears an empty or second condition, so as to more clearly indicate exhaustion of the volatile material 32. Most preferably, the image 14 is viewable when the dispenser 12 is full, empty, and at any point in between. However, the image 14 would be more readily viewable when the dispenser 12 is empty, in order to enhance the decorative nature in conjunction with dispenser 12 exhaustion. For purposes of the present invention, expiration of the volatile material 32 or system 10 refers to exhaustion of the volatile material 32.

When packaged dispenser 12 is filled (FIG. 7) with volatile material 32 and laminate 22 is adhered to the permeable membrane 24. There is virtually no diffusion of volatile material 32 when the dispenser is filled and laminate 22 covers membrane 24. Following removal of laminate 22, the system 10 begins to transition towards an empty or second condition. Of course, there may be a small amount of volatile material 32 that remains when the dispenser 12 is considered to have reached the second condition. As the volatile material 32 diffuses through the membrane 24, the membrane 24 slowly collapses upon the bottom wall 28. Following diffusion of the volatile material 32 across the membrane 24 there is less material 32 contained within dispenser 12. Virtually no new air enters the dispenser 12 subsequent to diffusion of volatile material 32. The result is a pressure gradient across the membrane 24, with a higher pressure existing in the ambient air than the pressure in dispenser 12. The pressure gradient causes the ambient air to exert a net positive pressure upon the dispenser, which presses the membrane 24 against the remaining volatile material 32 and ultimately the bottom wall 28. Continued diffusion of the volatile material 32 increases the force exerted upon the membrane 24, which causes the remaining volatile material to migrate from a center of wall 28 towards the periphery of wall 28. Continued migration and diffusion of the volatile material 32 results in an increasing surface area contact between membrane 24 and wall 28 until dispenser 12 is empty, or nearly empty. Increasing contact between the membrane 24 and the wall 28 allows for the image 14 to be more readily viewable. The pressure gradient ultimately resulting in migration of the volatile material 32 may also be viewed as occurring due to an increasing compressed vacuum presence within dispenser 12 as the volatile material continues to diffuse across membrane 24.

Referring to FIGS. 8–11, a small amount of volatile material 32 remains within the dispenser 12 when it is nearly empty, and is present in the form of a ring-like appearance towards the periphery of the bottom wall 28. A dye and thickener combine to comprise approximately 2% of the overall volatile material composition of the system 10 at the first condition. Preferably a higher concentration of dye is present in the volatile material 32 when the dispenser 12 is nearly empty, as the dye utilized does not easily diffuse across membrane 24. This results in a more readily viewable ring-like appearance. The color of the ring-like image is more intense in color than the coloration of the first condition because of the increased concentration of dye material. In the second condition the thickener and dye comprise nearly all of the material left within the dispenser 12. Of course, this may change dependant upon the particular dye composition and thickening agent utilized in the volatile material 32. As the system 10 approaches and is in a second condition, the nearly expired dispenser 12 can be seen so as to indicate its end of life.

When the dispenser 12 is full, or in the first condition, a decorative image may not be seen through the colored or opaque volatile material 32. As the dispenser 12 empties, or reaches the second condition, the decorative image 14 becomes viewable indicating a level of expiration, exhaustion, or use-up. Alternatively, the decorative image 14 may be viewable while the dispenser 12 is both full and empty. Indication of volatile material 32 exhaustion may be achieved by more readily viewing image 14 as a result of the absence of colored volatile material within the dispenser 12. Depending upon the specific volatile material composition, there may be numerous chemicals that either do not diffuse through the permeable membrane 24 or diffuse slower than the designed active ingredients or fragrances. Active ingredients may include chemicals such as esters, aldehydes, ketones, terpenes, alcohols, and aromatic compounds. As a result, material may be left within the blister 18 when it reaches a level of expiration in which replacement is necessary.

FIGS. 12–19 illustrate four material dispensing systems 10 that are alike in all respects but one to the system 10 of the foregoing FIGURES. The one difference between the systems of FIGS. 12–19 and the foregoing FIGURES are certain additions to frame 16 in each embodiment.

A small protrusion or protrusions have been added to the back of each frame 16 to support the back of the frame 16 in the event the frame 16 tips over. These protrusions are long enough to keep the membrane 24 away from the flat surface the frame 16 has tipped over on. The protrusions provide a space that is sufficient to let vapors from dispenser 12 diffuse thereby preventing or impeding marring to the surface. Without protrusions the vapor concentration could build up and mar the surface in a relatively short period of time. With protrusions, the membrane is spaced far enough from the flat surface to prevent or impede such damage. Where the membrane 24 and delicate surface are in direct contact marring occurs in a matter of hours or less. Protrusions permit an air passage that prevents damage all together or impedes marring from occurring for a matter of days or weeks. An increased time period from hours to days or weeks allows the user additional time to reposition the frame 16, in the event it is tipped over, prior to alteration or marring of a delicate surface To further reduce the possibility that the frame 16 will tip over, the protrusions along one edge of the frame 16 are disposed to support the frame 16 in its upright position. They extend outward from the frame 16, broadening the base upon which the frame 16 rests, thereby reducing the chance that the frame 16 will be tipped over at all.

Figure 14:
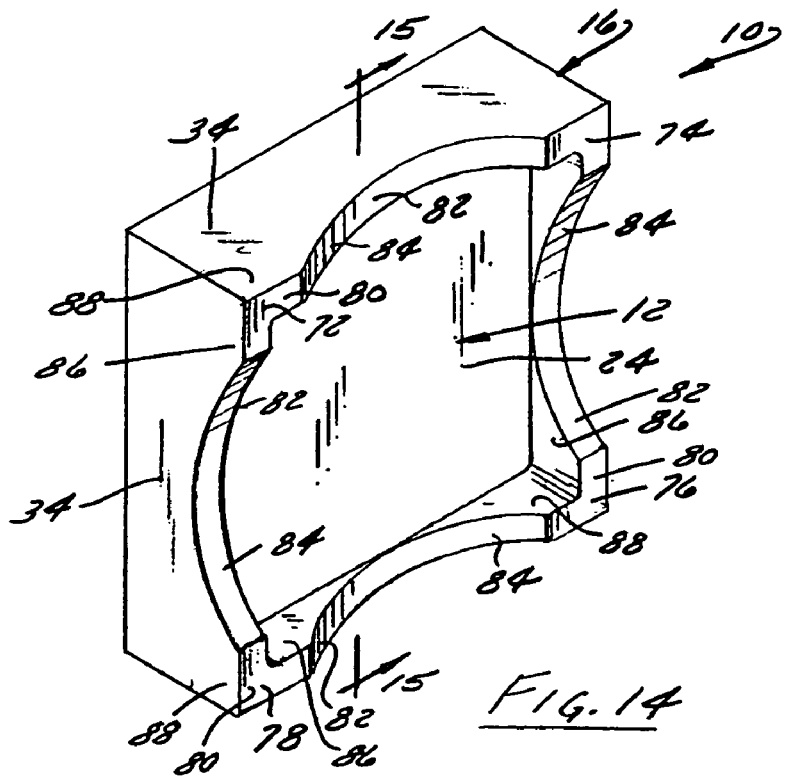
FIG. 14 is a back perspective view of the second embodiment of the invention.
Figure 15:
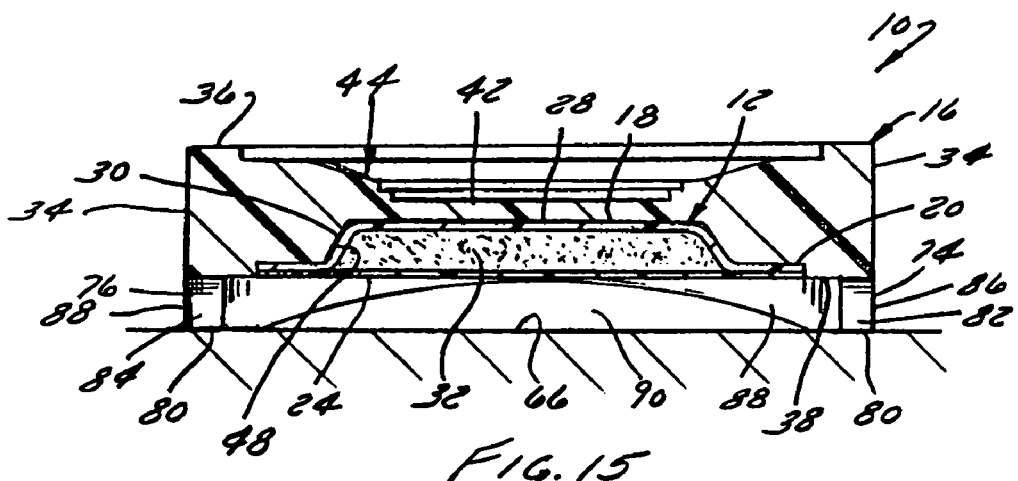
FIG. 15 is a sectional view of the second embodiment taken substantially along line 15—15 of FIG. 14.
Figure 16:
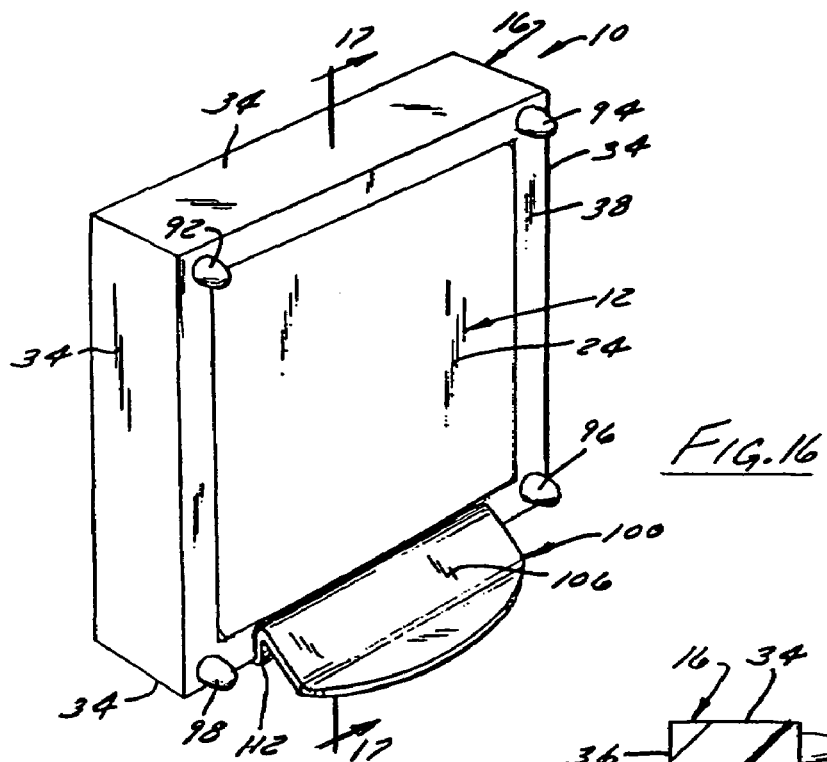
FIG. 16 is a back perspective view of the third embodiment of the invention.
Figure 17:
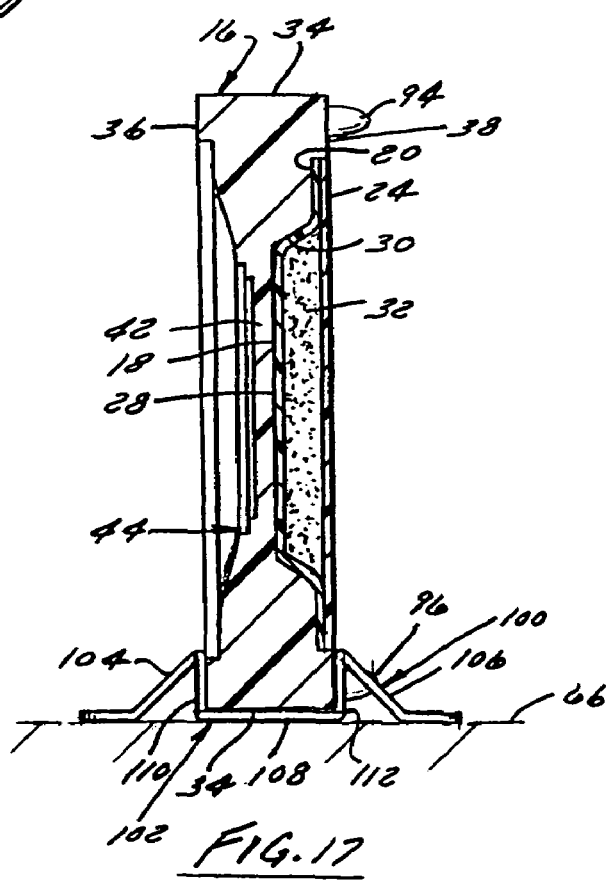
FIG. 17 is a sectional view of the third embodiment taken substantially along line 17—17 of FIG. 16.

While the protrusions are preferably formed integral with the base as shown in FIGS. 12–19, they may also be separately attached, as shown in the embodiment of FIGS. 16 and 17.

Figure 12:
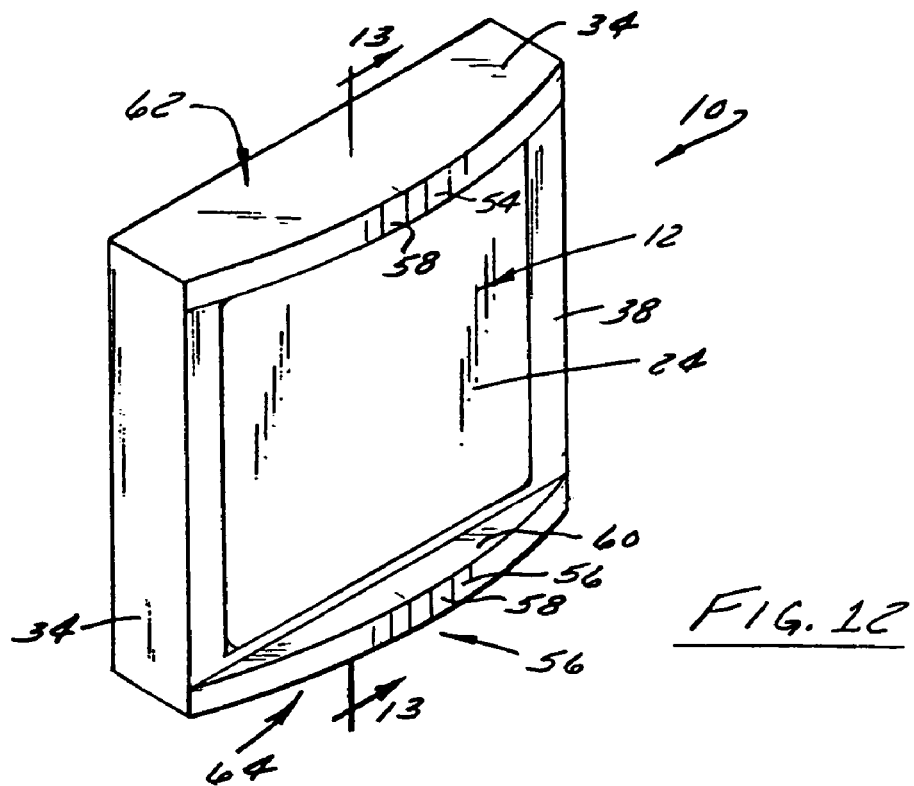
FIG. 12 is a back perspective view of the first embodiment of the invention.
Figure 13:
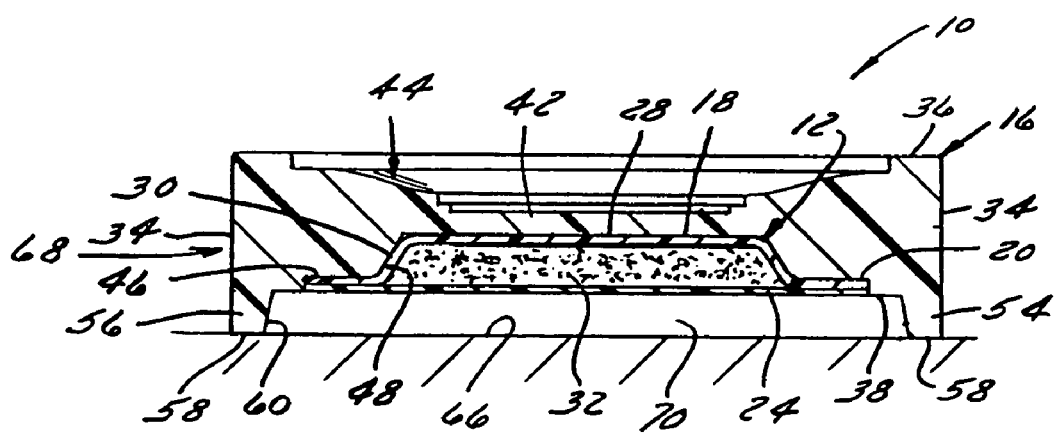
FIG. 13 is a sectional view of the first embodiment taken substantially along line 13—13 of FIG. 12.

Now referring to FIGS. 12 and 13, volatile material dispensing system 10 has protrusions 54, 56 extending laterally from the rear face 38 of frame 16. The protrusions 54, 56 have an arcuate edge 58, and a ledge 60. Protrusions 54, 56 are positioned opposite of one another proximal to a top end 62 and a bottom end 64. Preferably the projections 54, 56 extend the width of the frame 16 and are comprised of the same material as the frame 16. Alternatively, the projections 54, 56 may be comprised of other materials including metal alloys, various composite plastics, glass and the like.

The arcuate edge 58 preferably is convex, but may alternatively be concave in curvature. The arcuate edge 58 is preferably a curved structure disposed between two side walls 34. The protrusions 54, 56 preferably have a peak height between 3 and 8 mm. Most preferably, the protrusions 54, 56 have a height between 5.0 and 6.0 mm.

Ledge 60 is a substantially flat surface that extends from the rear face 38 to the arcuate edge 58. Placement of the protrusions 54, 56 upon the rear face 38 prevents tipping of the frame 16 onto the rear face 38 and acts as a supplemental support for the system 10. Most preferably the protrusions 54, 56 are placed upon the rear face 38, which increases the chances of the frame 16 tipping onto the front face 36 (i.e. away from the membrane 24 configured rear face 38). This is advantageous in the case where the delicate supporting surface 66 is uneven and may come into closer proximity to the membrane 24 than a substantially flat supporting surface 66. Alternatively, protrusions 54, 56 may extend laterally from both the rear face 38 and the front face 36. The protrusions 54, 56 are coplanar with the side walls 34 creating a continuous flat surface 68 for positioning on a supporting surface 66. The continuous flat surface 68 has a larger surface area than that of the side wall 34, which is useful for maintaining the system 10 in a desired upright and substantially vertical position.

Protrusions 54, 56 may be integrally formed with the frame 16 through an injection molding process. Protrusions 54, 56 may also be separately attached to the frame through a plurality of adhesive means, either permanently or releasably attached. An ethylene acrylin acid (EAA) copolymer may be used as an adhesive. In the event that the protrusions 54, 56 are releasably attached they may be reattached at any point.

When upright or substantially vertically disposed, the system 10 rests upon surface 68. When the frame 16 is in a horizontal position (FIG. 13), the frame 16 rests upon arcuate edge 58 of protrusions 54, 56. In the horizontal position the protrusions 54, 56 create an air passage 70 disposed between the membrane 24 and the supporting surface 66. Air passage 70 prevents the build-up of concentrated gases harmful to the surface 66, and permits diffusion of the volatile material 32. The air passage 70 approximately has the same height of the protrusions 54, 56 and a width approximately the same as the frame 16.

Now referring to FIGS. 14 and 15, volatile material dispensing system 10 has four protrusions 72, 74, 76, 78. Protrusions 72, 74, 76, 78 have a base surface 80, curved side walls 82, 84 and flat side walls 86, 88. The protrusions 72, 74, 76, 78 preferably have a height of between 3 to 7 mm.

The base surface 80 is positioned proximal to each of the four corners of the frame 16. Base surface 80 has a flat surface and is substantially L-shaped. The flat side walls 86, 88 are preferably disposed in a coplanar relationship with the side walls 34 of the frame 16 to provide a continuous flat surface. Curved side wall 82 extends from the base surface 80 and couples to an adjacent side wall 84. Curved side walls 82, 84 have a preferred width of between 3 and 5 mm.

When the system 10 is tipped over and horizontally disposed the protrusions 72, 74, 76, 78 provide for a solid base and prevent any further tipping. The four base surfaces 80 are coplanar, which prevents tipping when the system 10 is in a horizontal position. The air passages 90 prevent concentrated build-up of gases that are harmful to a delicate supporting surface 66. The air passages 90 permit proper ventilation and diffusion of the volatile material 32 when the system 10 is horizontally displaced. Air passage 90 is approximately the same height as that of the protrusions 72, 74, 76, 78, and is preferably equal to or greater than 5.0 mm.

Referring to FIGS. 16 and 17, volatile material dispensing system 10 has four protrusions 92, 94, 96, 98 and a base clamp 100. The protrusions 92, 94, 96, 98 have a bulbous shape and may also be referred to as nodules 92, 94, 96, 98. The nodules 92, 94, 96, 98 are disposed proximal to each of the four corners of the frame 16. Preferably the nodules 92, 94, 96, 98 have a height of between 5 and 8 mm. Nodules 92, 94, 96, 98 are positioned approximately 2–3 mm from the side walls 34 of the frame 16. Furthermore, the nodules 92, 94, 96, 98 are preferably disposed on the rear face 38. Frame 16 may be used in the absence of base clamp 100 and continue to prevent alteration of base surface 66.

The base clamp 100 includes a C-shaped clip 102 and two protrusions 104, 106. The C-shaped clip 102 has a bottom wall 108 and two side walls 110, 112. Side walls 110, 112 are attached respectively to protrusions 104, 106. Protrusions 104, 106 extend laterally from the clamp 100 to a supporting surface 66. The protrusions 104, 106 preferably have a length of between 10 and 30 mm, with a width of preferably between 30 and 40 mm. The base clamp 100 is preferably between 5 and 10 mm in height, has an overall depth preferably between 40 and 60 mm, and a width preferably between 30 and 40 mm. The base clamp 100 holds the frame 16 and may also be referred to as a supplemental support member 100.

The distance between side walls 110, 112 is slightly larger than the width of the frame 16. The clip 102 receives the frame 16, whereby the bottom wall 106 is in direct contact with a side wall 34. Front face 36 is in direct contact with side wall 110 and rear face 38 is in direct contact with side wall 112. The frame 16 is centrally positioned into the clamp 100. Alternatively, the base clamp 100 may be a spring clip, other mechanical means or utilize adhesive configured to hold the frame 16 in place. The base clamp 100 maintains the relative vertical position of the system 10. If the frame 16 should be tipped over where the rear face 38 is proximal to the supporting surface 66, the nodules 92, 94 will distance the membrane 24 from the delicate surface 66. An air passage (not shown) is positioned between the membrane 24 and the supporting surface 66.

Figure 18:
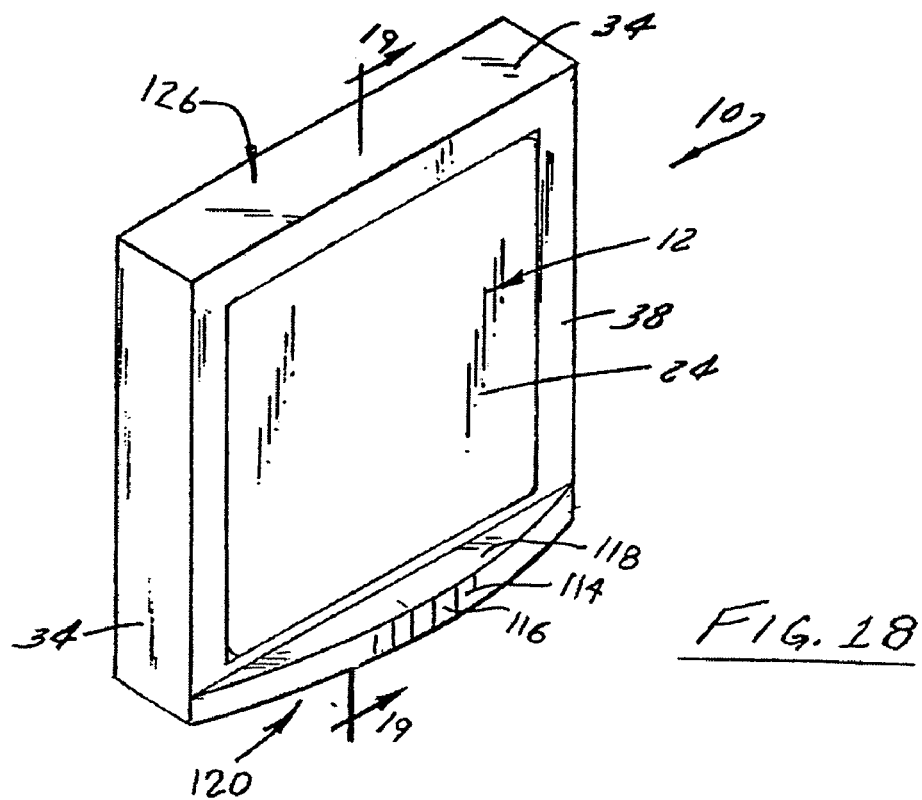
FIG. 18 is a back perspective view of the fourth embodiment of the invention.
Figure 19:
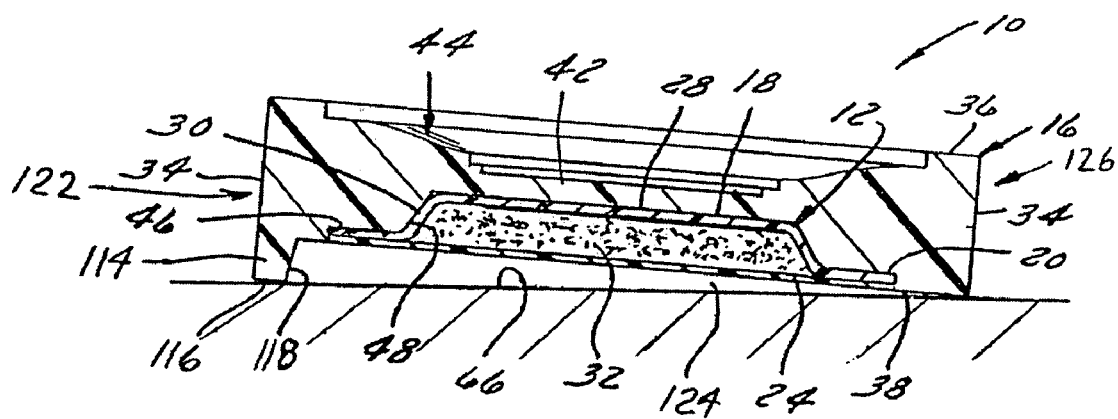
FIG. 19 is a sectional view of the fourth embodiment taken substantially along line 19—19 of FIG. 18.

Now referring to FIGS. 18 and 19, volatile material dispensing system 10 has protrusion 114 extending laterally from the rear face 38 of frame 16. The protrusion 114 has an arcuate edge 116, and a ledge 118. Protrusion 114 is positioned proximal to a bottom end 120. Preferably the projection 114 extends the width of the frame 16 and is comprised of the same material as the frame 16. Alternatively, the projection 114 may be comprised of other materials including metal alloys, various composite plastics, glass and the like.

Arcuate edge 116 is preferably a curved structure disposed between two side walls 34. The arcuate edge 116 preferably is convex, but may alternatively be concave in curvature. Protrusion 114 preferably has a peak height between 3 and 10 mm. Most preferably, the protrusion 114 has a height between 5.0 and 7.0 mm.

Ledge 118 is a substantially flat surface that extends from the rear face 38 to the arcuate edge 116. Placement of the protrusion 114 upon the rear face 38 prevents tipping of the frame 16 onto the rear face 38 and acts as a supplemental support for the system 10. Most preferably the protrusion 114 is placed upon the rear face 38, which increases the chances of the frame 16 tipping onto the front face 36 (i.e. away from the membrane 24 configured rear face 38). This is advantageous in the case where the delicate supporting surface 66 is uneven and may come into closer proximity to the membrane 24 than a substantially flat supporting surface 66. Alternatively, protrusion 114 may extend laterally from both the rear face 38 and the front face 36. The protrusion 114 is coplanar with the side walls 34 creating a continuous flat surface 122 for positioning on a supporting surface 66. The continuous flat surface 122 has a larger surface area than that of the side wall 34, which is useful for maintaining the system 10 in a desired upright and substantially vertical position. Positioning of a protrusion merely upon a front face would permit a frame to tip over upon the side proximal to an emanating surface with greater ease and would not provide an air passage once tipped over.

Protrusion 114 may be integrally formed with the frame 16 through an injection molding process. Protrusion 114 may also be separately attached to the frame through a plurality of adhesive means, either permanently or releasably attached. An ethylene acrylin acid (EAA) copolymer may be used as an adhesive. In the event that the protrusion 114 is releasably attached it may be reattached at any point.

When upright or substantially vertically disposed, the system 10 rests upon surface 122. When the frame 16 is in a semi-horizontal or substantially horizontal position (FIG. 19), the frame 16 rests both upon arcuate edge 116 and the rear face 38 proximal to the top end 126. While in a substantially horizontal position the protrusion 114 creates an air passage 124 disposed between the membrane 24 and the supporting surface 66. Air passage 124 hinders the build-up of concentrated gases harmful to the surface 66, and permits diffusion of the volatile material 32. Air passage 124 has a variable height dependent upon proximity to the protrusion 114 and a width approximately the same as the frame 16. Proximal to protrusion 114 the air passage has approximately the same height as the protrusion 114.

In the event the system 10 tips over backwards, a protrusion 114 impedes marring or alteration of a delicate surface 66 through air passage 124. Air passage 124 hinders the build-up of concentrated gases and fumes that may cause marring or alteration to the surface 66. This hindrance permits a substantial period of time before marring, if any, occurs as compared to a frame (not shown) without a protrusion disposed upon a face proximal to a dispensing or emanating surface. Alteration or marring that may occur is dependant upon the particular chemical composition of volatile material 32. Direct contact between a membrane 24 and delicate surface 66 would cause alteration of the surface 66 in most cases less than an hour. The presence of protrusion 114 impedes alteration of the surface 66 for days and in some cases prevents alteration all together. A greater amount of time is present for the user to reposition a frame 16 that may have been inadvertently tipped over.

The volatile material 32 may contain various chemical compositions that are harmful to treated and untreated surfaces. Perfumes and air fresheners are known to contain chemicals such as esters, aldehydes, ketones, terpenes, alcohols, and aromatic compounds, all of which may cause deleterious effects to delicate surfaces. Such effects also include marring and altering the surface composition and appearance. Concentration of gases that have emanated from the volatile material will contain an increased concentration of chemicals that are harmful to delicate surfaces, as the concentration increases the harmful effects will be more severe and take less time to cause such harmful effects. Volatile material gases have a greater concentration in immediate proximity to the dispenser 12. In order for the dispenser 12 to function as it is designed, molecules of the active ingredient must diffuse from the region of increased concentration to regions of lesser concentration. The build-up of gases increases the concentration of the chemicals that are harmful to delicate surfaces. Delicate surfaces may include fine furniture and various other treated surfaces not designed to resist chemical deterioration and alteration. If the build-up is in direct contact with the delicate surfaces, a breakdown or marring of the surface will result.

In conjunction with a decorative display frame utilized for disposing a membrane based volatile material dispenser, a protrusion or protrusions (FIGS. 12–19) on at least one face of the dispenser prevent and/or impede concentration of harmful gases. Preferably the protrusions are disposed on the same side of the frame 16 that the dispenser 12 is attached. The protrusions provide for an air passage between the membrane surface and the delicate surface 66. By adequately spacing the membrane 24 from the delicate surface 66, the gaseous volatile material properly diffuses into the ambient atmosphere, thereby preventing a concentrated build-up. An air passage permitted by the protrusions is sufficient to prevent and/or impede damage to the supporting surface 66 from direct or close contact to the membrane 24.

The protrusions (FIGS. 12–19) are displaced in such a manner as to prevent the system 10 from tipping over from a vertically disposed position. The protrusions increase the stability of the system 10 upon a supporting surface 66. This enables the system 10 to be less likely to tip over to a horizontal displacement. Protrusions prevent or impede the harmful effects of chemicals emanating from a dispenser 12 when the system 10 is horizontally or semi-horizontally displaced. A build-up of concentrated gases is prevented and/or hindered by the protrusions and thereby prevents or impedes marring or alteration of the delicate supporting surface 66.

It is understood that the present invention is not limited to the embodiments described above and illustrated herein, but encompasses any and all variations falling within the scope of the appended claims.

INDUSTRIAL APPLICABILITY

The invention provides an improved dispensing system for dispensing volatile materials into the ambient air.

We claim:

1. A volatile material dispensing system, comprising:
a reservoir having a first surface and a vapor permeable membrane sealed to an outer periphery of said first surface;
a volatile material contained within said reservoir, wherein said volatile material is diffused through said membrane into an ambient atmosphere;
a planar frame having a front face and a rear face, wherein said reservoir is affixed to one of the front face and the rear face of said frame and said membrane is coplanar with said one of the front face and the rear face; and
a plurality of protrusions attached to and extending laterally from said one of the front face and the rear face of said frame, wherein said protrusions are configured to distance said membrane from a supporting surface when said one of the front face and the rear face is horizontally disposed adjacent the supporting surface, thereby providing an air passage sufficient to prevent volatile material gases from altering said supporting surface.

2. The system according to claim 1 wherein said system further comprises a removable vapor impermeable laminate covering said vapor permeable membrane to prevent diffusion of said volatile material.

3. The system according to claim 2 wherein said reservoir is an evacuatable blister that transitions from a first filled condition to a second collapsed condition.

4. The system according to claim 1 wherein said volatile material is selected from the group consisting of air fresheners, fragrances, and insecticides.

5. The system according to claim 1 wherein said plurality of protrusions provide an air passage with a height no less than 3.0 mm.

6. The system according to claim 1 wherein said plurality of protrusions have a height of between 3 and 12 mm.

7. The system according to claim 1 wherein said plurality of protrusions include four protrusions.

8. The system according to claim 7 wherein said frame is rectangular and translucent.

9. The system according to claim 8 wherein said frame has four corners and each of said corners has a corresponding one of said plurality of protrusions.

10. The system according to claim 1 wherein said plurality of protrusions include two protrusions.

11. The system according to claim 10 wherein said protrusions are arcuately shaped and disposed at opposite sides of said frame.

12. The system according to claim 11 wherein said frame is rectangular and translucent.

13. The system according to claim 11 wherein a bottom surface of said protrusions is positioned to support said frame both when said frame is in a substantially upright and a substantially horizontal position.

14. A volatile material dispenser comprising
a planar frame configured to support a reservoir containing a volatile material enclosed by a vapor permeable membrane having a bottom surface coplanar with a rear face of said frame;
a plurality of protrusions disposed on the rear face of said frame, wherein said protrusions are configured to distance said frame from a supporting surface when the membrane is horizontally disposed adjacent the supporting surface and to provide an air passage sufficient to prevent volatile material gases from altering said supporting surface; and
wherein said frame is rectangular and has four corners.

15. The dispenser according to claim 14 wherein said plurality of protrusions include two protrusions.

16. The dispenser according to claim 15 wherein said plurality of protrusions have a height between 3 and 12 mm.

17. The dispenser according to claim 14 wherein said plurality of protrusions include four protrusions, each of said corners has a corresponding one of a plurality of protrusions.

18. The dispenser according to claim 17 wherein each protrusion has a bottom surface that is coplanar with a bottom surface of each other protrusion.

19. A volatile material dispenser, comprising:
a reservoir configured to dispense a volatile material;
a planar frame having a front face and a rear face, wherein said frame is configured to support said reservoir, wherein said volatile material is enclosed by a vapor permeable membrane;
a plurality of protrusions disposed on at least one of the front face and the rear face of said frame, wherein said protrusions are configured to distance said membrane from a supporting surface when said membrane is horizontally disposed adjacent said supporting surface to provide an air passage sufficient to prevent volatile material gases from altering said supporting surface; and
a supplemental support member attached to said frame for maintaining the relative position of said frame and preventing tipping of said frame.

20. The dispenser according to claim 19 wherein said plurality of protrusions have a height of between 3 and 12 mm.

21. The dispenser according to claim 20 wherein said frame is translucent, rectangular, and has four corners.

22. The dispenser according to claim 21 wherein said one face is the rear face of said frame and wherein said plurality of protrusions include two protrusions.

23. The dispenser according to claim 22 wherein said plurality of protrusions are arcuately shaped.

24. The dispenser according to claim 21 wherein said one face is the rear face of said frame and said plurality of protrusions include four protrusions, each of said corners has a corresponding one of a plurality of protrusions.

25. A volatile material dispensing system, comprising:
a reservoir having a first surface and a vapor permeable membrane sealed to an outer periphery of said first surface;
a volatile material contained within said reservoir, wherein said volatile material is diffused through said membrane into an ambient atmosphere;
a planar frame having a front face and a rear face, wherein said reservoir is affixed to said rear face of said frame; and
a protrusion attached to said rear face of said frame, wherein said protrusion is configured to distance said membrane from a supporting surface when said membrane is disposed adjacent the supporting surface and is in a substantially horizontal position providing an air passage sufficient to impede volatile material gases from altering said supporting surface.

26. The system according to claim 25 wherein said system further comprises a removable vapor impermeable laminate covering said vapor permeable membrane to prevent diffusion of said volatile material.

27. The system according to claim 26 wherein said reservoir is an evacuatable blister that transitions from a first filled condition to a second collapsed condition.

28. The system according to claim 25 wherein said volatile material is selected from the group consisting of air fresheners, fragrances, and insecticides.

29. The system according to claim 28 wherein said frame is rectangular and translucent.

30. The system according to claim 29 wherein said protrusion is arcuately shaped.

31. The system according to claim 30 wherein said frame is selected from the group of compositions including glass, injection-molded plastic, and copolyester resin.

32. The system according to claim 29 wherein a bottom surface of said protrusion is positioned to support said frame in a substantially upright position.

33. The system according to claim 32 wherein said bottom surface is substantially coplanar with a side wall of said frame.

34. The system according to claim 25 wherein said protrusion provides an air passage having a peak height no less than 3.0 mm.

35. The system according to claim 25 wherein said protrusion has a height of between 3 and 12 mm.

* * * * *